United States Patent [19]

Cruickshank et al.

[11] 4,434,182
[45] Feb. 28, 1984

[54] INSECTICIDAL SUBSTITUTED-BIPHENYLMETHYL OXIME ETHERS

[75] Inventors: Philip A. Cruickshank, Princeton; Thomas G. Cullen, Plainsboro, both of N.J.

[73] Assignee: FMC Corporation, Philadelphia, Pa.

[21] Appl. No.: 438,108

[22] Filed: Nov. 1, 1982

[51] Int. Cl.³ .................... A01N 33/24; C07C 131/00
[52] U.S. Cl. ..................................... 424/327; 564/256
[58] Field of Search ......................... 564/256; 424/327

[56] References Cited

U.S. PATENT DOCUMENTS

Re. 30,634  6/1981  Henry ................................. 564/256

FOREIGN PATENT DOCUMENTS 4754  10/1979  European Pat. Off. .

Primary Examiner—Natalie Trousof
Assistant Examiner—L. Hendriksen

Attorney, Agent, or Firm—Robert M. Kennedy; H. Robinson Ertelt; Robert L. Andersen

[57] ABSTRACT

Oxime ethers of the formula

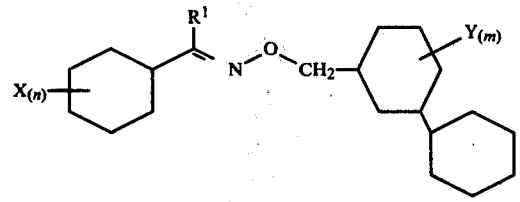

wherein $R^1$ is isopropyl, cyclopropyl, cyclopropylmethyl, or cyclobutyl; X and Y are independently halogen or straight or branched chain alkyl or alkoxy of 1 to 4 carbon atoms optionally substituted with one or more halogen atoms; n is 0–2; and m is 1–4 are disclosed. The insecticidal efficacy and preparation of the compounds are described and exemplified.

9 Claims, No Drawings

INSECTICIDAL SUBSTITUTED-BIPHENYLMETHYL OXIME ETHERS

This invention pertains to the field of insecticides; more specifically, it pertains to insecticidal/acaricidal (substituted-[1,1'-biphenyl]-3-yl)methyl ether-derivatives of certain (aryl) (cycloalkyl/alkyl) ketoximes. The insecticidal oxime ethers of this invention are compounds of formula I

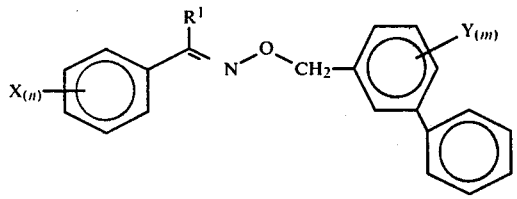

wherein the substituent groups are as hereinafter defined.

Various oxime ethers of general formula A have previously been reported as having insecticidal properties.

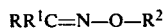

$$RR^1C=N-O-R^2 \quad A$$

U.S. Pat. No. 4,079,149, issued Mar. 14, 1978, discloses as insecticides/acaricides oxime ethers of formula A wherein R is optionally substituted phenyl, $R^1$ is optionally substituted alkyl, alkenyl, or cyclopropyl, and $R^2$ is 3-phenoxybenzyl. The E isomers of the disclosed compounds are reported to be more active than the corresponding Z isomers.

German Offenlegungschrift No. 2,806,664 [Chemical Abstracts 90, 22561u (1979)], published Aug. 24, 1978, discloses insecticidal compounds of formula A wherein R is substituted aryl or alkyl, $R^1$ is optionally substituted cycloalkyl, and $R^2$ is a group of the formula

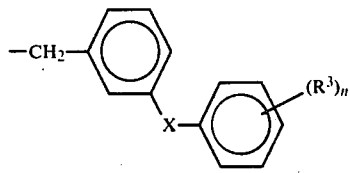

in which X is oxygen or methylene, $R^3$ is hydrogen, halogen, alkyl, or alkoxy, and n is 1-5.

Japanese Kokai No. 54-138,532 [Derwent Abstract 183,458/49], published Oct. 27, 1979, describes a series of oxime ethers of formula A wherein R is optionally substituted phenyl, $R^1$ is alkyl, cycloalkyl, haloalkyl, alkenyl, or alkynyl, and $R^2$ is a radical of the formula

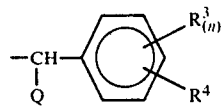

in which Q is hydrogen or cyano, $R^3$ is hydrogen or alkyl, n is 1 or 2, and $R^4$ is alkenyl, cycloalkenyl, or a group

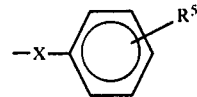

in which X is oxygen, sulfur, or methylene, and $R^5$ is hydrogen, halogen, or alkyl. The compounds are disclosed as insecticides/miticides having immediate and residual activity.

Japanese Kokai No. 55-115,864 [Derwent Abstract 74409C/42], published Sept. 6, 1980, discloses as insecticides/acaricides oxime ethers of formula A wherein R is optionally substituted phenyl, $R^1$ is alkyl, and $R^2$ is 3-phenoxybenzyl or 5-benzylfurylmethyl. These compounds are described by Nanjyo et al. in *Agric. Biol. Chem.* 44, 217 (1980) as possessing pyrethroid-like actions.

German Offenlegungschrift No. 2,926,408, published Jan. 17, 1980, discloses oxime ether insecticides of formula A wherein R is optionally substituted aryl or alkyl, $R^1$ is optionally substituted cycloalkyl, alkyl, or alkenyl, and $R^2$ is a 2,6-dihalobenzyl radical.

A large series of oxime ethers of formula A is disclosed in European Patent Application Publication No. 4,754, published Nov. 17, 1979. In these compounds, R is selected from a wide range of optionally substituted aromatic or hetero-aromatic radicals, $R^1$ is optionally substituted alkyl, cycloalkyl, or alkenyl, and $R^2$ is optionally substituted furylmethyl or thienylmethyl, allethrolonyl or the like, phthalimidomethyl or a hydrogenated derivative thereof, 4-phenyl-2-butynyl, 4-phenyl-2-butenyl optionally substituted at C-3, or optionally substituted benzyl having up to three ring substituents two of which are independently selected from halogen, alkyl, alkenyl, alkynyl, methylenedioxy, haloalkyl, haloalkenyl, and cyano, and the third being a —ZY group in which Z is oxygen, sulfur, or methylene, and Y is hydrogen, alkyl, alkenyl, alkynyl, or optionally substituted phenyl.

Also known in the art are a number of insecticidal-/acaricidal pyrethroid esters in which the alcohol moiety is an optionally substituted [1,1'-biphenyl]-3-methyl alcohol residue. Various such compounds are disclosed in U.S. Pat. Nos. 4,130,657; 4,214,004; 4,238,505; 4,329,518; and 4,341,796; and European Patent Application Publication No. 49,977, published Apr. 21, 1982, corresponding to copending application U.S. Ser. No. 265,940, filed May 21, 1981.

In this application "halogen" or "halo" means fluorine, chlorine, or bromine, and "haloalkyl" means an alkyl group substituted with one or more halogen atoms. The term "insecticide" or "insecticidal compound" is used in its broadest sense and includes compounds possessing activity against true insects, acarids, or other household, veterinary, or crop pests of the phylum arthropoda.

The insecticidal compounds of this invention are oxime ethers of formula I

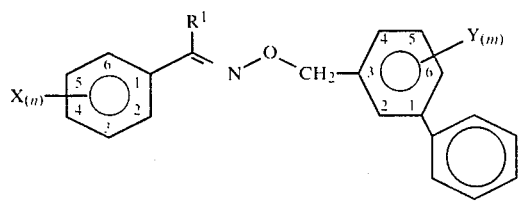

wherein $R^1$ is isopropyl, cyclopropyl, cyclopropylmethyl, or cyclobutyl; X and Y are independently halogen or straight or branched chain alkyl or alkoxy of 1 to 4 carbon atoms optionally substituted with one or more halogen atoms; n is 0–2; and m is 1–4. When n is 2, each X substituent may be selected independently of the other. Likewise, when m is 2–4, each Y substituent may be independently selected.

As with oxime ethers generally, the compounds of formula I exhibit geometrical isomerism and, therefore, exist in two isomer forms, the E or anti-form and the Z or syn form. The E isomer form differs from the Z form in that the oxime oxygen is trans to the phenyl ring on the double bond, rather than cis. The E isomer form is depicted in formula I. The present E isomers are substantially more active insecticidally than the corresponding Z isomers and are, therefore, preferred embodiments of the present invention, as are EZ mixtures having a high isomeric excess of the E isomer over the Z isomer.

Preferred embodiments with respect to individual substituent groups are as follows:
—$R^1$: cyclopropyl.
—X: halogen, especially chlorine or fluorine; straight or branched chain alkyl of 1 to 4 carbon atoms, advantageously of 1 to 3 carbon atoms; haloalkyl of 1 or 2 carbon atoms such as fluoroalkyl, particularly trifluoromethyl; the group $OCFZ^1Z^2$ wherein $Z^1$ and $Z^2$ are independently hydrogen or fluorine.
—Y: halogen such as fluorine; alkyl of 1 to 4 carbon atoms, especially methyl.

Advantageously, n is 1 and the X substituent is positioned at C-4 of the phenyl ring. Where n is 2, X is preferably placed at the C-2 and C-4 positions. The preferred placement for Y generally depends upon the nature of the substituent group. For example, when Y is methyl, a preferred embodiment, m is advantageously 1 or 2, especially 1, and Y is preferably positioned at C-2 or at C-2 and C-4. When Y is a halogen such as fluorine, m is generally 2–4, and Y is advantageously placed at C-2 and C-6 where m is 2 and at C-2, C-4, and C-6 where m is 3.

A particularly desirable sub-genus of the present invention comprises the oxime ethers of formula II

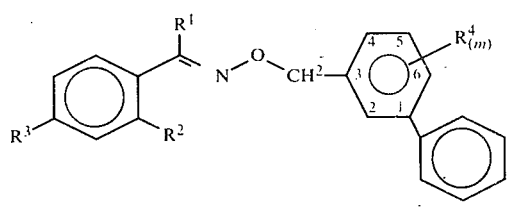

wherein $R^1$ is isopropyl, cyclopropyl, cyclopropylmethyl, or cyclobutyl; $R^2$ is hydrogen, halogen, or alkyl of 1 to 4 carbon atoms; $R^3$ is hydrogen, halogen, straight or branched chain alkyl of 1 to 4 carbon atoms, haloalkyl of 1 or 2 carbon atoms, or the group —$OCFZ^1Z^2$ wherein $Z^1$ and $Z^2$ are independently hydrogen or fluorine, and $R^4$ is alkyl of 1 to 4 carbon atoms and m is 1 or 2, or $R^4$ is halogen and m is 2 to 4; with the proviso that when $R^1$ is isopropyl, then m is 1 and $R^4$ is alkyl, preferably methyl, and is positioned at the C-2 carbon atom.

A preferred class within this sub-genus is comprised of the compounds wherein $R^1$ is isopropyl, cyclopropyl or cyclobutyl; $R^2$ is hydrogen, chlorine, or methyl; $R^3$ is hydrogen, halogen, straight or branched chain alkyl of 1 to 4 carbon atoms, fluoroalkyl of 1 or 2 carbon atoms, or the group —$OCFZ^1Z^2$ wherein $Z^1$ and $Z^2$ are independently hydrogen or fluorine; m is 1 or 2; and $R^4$ is methyl and is positioned at the C-2 or C-2 and C-4 carbon atoms; with the proviso that m is 1 when $R^1$ is isopropyl. Advantageously, each of $R^2$ and $R^3$ is hydrogen or chlorine, or $R^2$ is hydrogen and $R^3$ is chlorine, fluorine, straight or branched chain alkyl of 1 to 4 carbon atoms, trifluoromethyl, difluoromethoxy, or trifluoromethoxy. The compounds of this preferred class are particularly interesting in that they generally show good activity against both acarids and true insects.

The compounds characterized by superior overall insecticidal activity are those in which $R^1$ is isopropyl or cyclopropyl, particularly cyclopropyl; $R^2$ is hydrogen; $R^3$ is chlorine, fluorine, straight or branched chain alkyl of 1 to 3 carbon atoms, trifluoromethyl, difluoromethoxy, or trifluoro methoxy; m is 1; and $R^4$ is methyl and is positioned at the C-2 carbon atom. The compound wherein $R^1$ is cyclopropyl and $R^3$ is trifluoromethoxy also gives superior soil incorporated residual activity against corn rootworm, and the compound in which $R^1$ is cyclopropyl and $R^3$ is chlorine, fluorine, ethyl, isopropyl, or trifluoromethoxy also has good upward systemic insecticidal activity.

The present oxime ethers may be prepared by methods described in the literature for similar compounds. One such method employed herein is similar to the method described in U.S. Pat. No. 4,079,149 and involves the reaction of an appropriate oxime with an appropriately substituted biphenylmethyl halide in the presence of sodium hydride and a solvent mixture of dimethylformamide and toluene, as illustrated in the following equation:

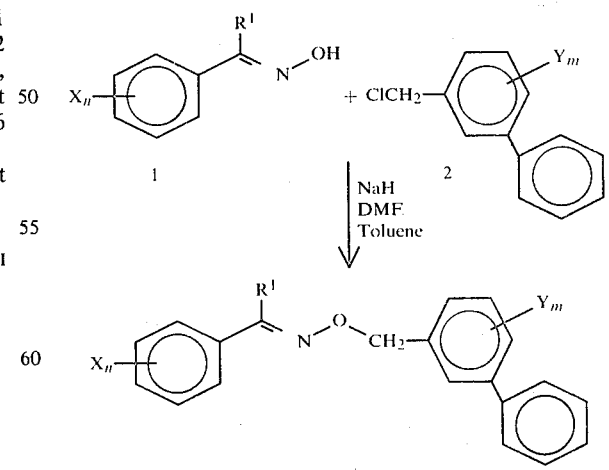

This method is described more fully in Example 2 below. In a variation of this method, the coupling reaction was effected with powdered potassium hydroxide and tetrabutylammonium bromide in tetrahydrofuran, as described in Example 17 below. In a further method for preparing the present oxime ethers, an alkali metal salt of the oxime is produced first then allowed to react with the substituted-biphenylmethyl halide in a suitable solvent. This last method is similar to General Procedure F in European Patent Publication No. 4,754, published Oct. 17, 1979, and is described more fully in Example 1C below. In all three methods, the isomeric integrity of the starting material oxime remains essentially intact in the conversion, and the highly desirable E isomer of the oxime ether product is obtained merely by employing the E-oxime isomer as the starting material.

The intermediate oximes may be prepared in the usual manner from the corresponding ketones by reaction with hydroxylamine hydrochloride. The oximes so produced are in the form of EZ mixtures which may be converted to 98% or greater E isomer by the method of J. H. Paul, U.S. Pat. No. 4,158,015. The stereo-selective conversion is effected by treating a solution of the EZ mixture in an organic solvent with a protic or Lewis acid, under anhydrous conditions, to precipitate the E isomer of an immonium complex and neutralizing the precipitate with a dilute organic/inorganic base such as sodium carbonate or sodium bicarbonate. Reaction conditions employed herein for this conversion are given in Examples 1B and 5B below. Alternatively, it may be possible to separate the E oxime from the EZ mixture, for example by crystallization, as described in Example 17 below.

The ketone precursors to the oximes are either commercially available or may be prepared by methods known in the art or by methods analogous to known methods. The methods illustrated in the chemical equations below were found to be particularly useful.

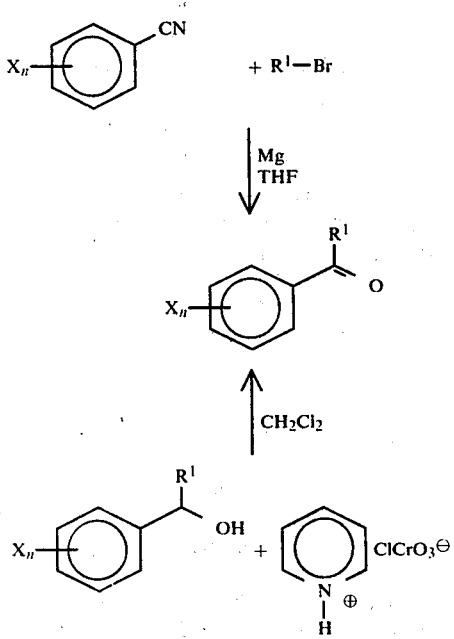

The illustrated methods are adaptations from the literature. The first method, the addition of a Grignard reagent to the cyano group of an aromatic nitrile, is discussed generally in *Organic Chemistry*, N. L. Allinger et al., Eds., Worth Publishers, Inc., New York, 1971, chapter 21, p. 586. The chlorochromate oxidation method is similar to that described by E. J. Corey and J. W. Suggs, *Tetrahedron Letters*, 31, 2647 (1975).

The substituted-biphenylmethyl halide intermediates, or substituted-biphenylmethanol precursors to them, are either known in the art or are similar to known compounds, and may be prepared by previously described methods or modifications thereof. See, for example, Examples 19-22 of U.S. Pat. No. 4,238,505 and Methods A, G, H, I, J, K, L, and M described in U.S. Pat. No. 4,329,518, incorporated herein by reference.

In particular, 2-methyl[1,1'-biphenyl]-3-methanol may be prepared by Method G of U.S. Pat. No. 4,329,518, 2,4-dimethyl[1,1'-biphenyl]-3-methanol by Method H, and 2,6-difluoro[1,1'-biphenyl]-3-methanol, 2,4,6-trifluoro[1,1'-biphenyl]-3-methanol, and 2,4,5,6-tetrafluoro[1,1'-biphenyl]-3-methanol by Method I of the same patent. The 3-methanol compounds are readily converted into the 3-chloromethyl derivatives by treatment with thionyl chloride in the presence of pyridine and toluene. Also, treatment of the alcohols with hydrogen bromide in concentrated sulfuric acid, as described for primary alcohols generally in *Organic Synthesis*, Coll. Vol. 1, 2nd Ed., 25 (1938), will give the corresponding 3-bromomethyl compounds.

An additional method for preparing the intermediate 3-chloromethyl-2-methyl[1,1'-biphenyl] involves a Sommelet-Hauser rearrangement of N,N,N-trimethyl[1,1'-biphenyl]-2-methanaminium iodide to give 3-dimethylaminomethyl-2-methyl-[1,1'-biphenyl], which is then converted into the 3-chloromethyl derivative by treatment with ethyl chloroformate. The N,N,N-trimethyl-[1,1'-biphenyl]-2-methanaminium iodide starting material may be prepared in four steps from 2-biphenylcarboxylic acid via the acid chloride, dimethyl carboxamide, and dimethylaminomethyl derivatives.

The examples which follow illustrate preparation of the oxime ethers of this invention in accordance with the methods described above. Unless otherwise indicated, all temperatures are in degrees Celsius, all pressures are in millimeters of mercury, and reduced pressure for concentrations of liquid was produced by a water aspirator. Proton chemical shifts, taken from nmr spectra in CDCl$_3$, are reported in ppm with respect to tetramethylsilane. In peak descriptions from nmr spectra, "s" means singlet, "d" means doublet, "m" means multiplet, "t" means triplet, and "q" means quartet.

The starting material ketones for Examples 1-8, 11, 13, 15 and 16 were obtained from commercial sources. The ketones for Examples 9, 10, 17, and 18 were prepared by a Grignard addition to an aromatic nitrile. This method is fully described in Example 17 below. For Examples 12 and 14, the ketones were prepared by the chlorochromate oxidation method described above.

EXAMPLE 1

Synthesis of
(E)-(4-chlorophenyl)(cyclopropyl)methanone
O-[(2-methyl[1,1'-biphenyl]-3-yl)methyl]oxime A. Preparation of
(E,Z)-(4-chlorophenyl)(cyclopropyl)methanone oxime In a manner similar to that described in *Organic Synthesis*, Coll. Vol. 2, 2nd Ed., 70 (1938), the reaction of 25.0 g (0.138 mole) of (4-chlorophenyl)(cyclopropyl) ketone, 15.0 g (0.216 mole) of hydroxylamine hydrochloride, 27.6 g (0.69 mole) of sodium hydroxide, 50 ml of ethanol, and 9 ml of water produced 11.7 g of (E,Z)-(4-chlorophenyl)(cyclopropyl)methanone oxime.

The nmr spectrum was consistent with the proposed structure.

B. Preparation of (E)-(4-chlorophenyl)(cyclopropyl)methanone oxime

In a manner similar to that of Example 1 of U.S. Pat. No. 4,158,015, 25.42 g (0.13 mole) of (E,Z)-(4-chlorophenyl)(cyclopropyl)methanone oxime was dissolved in 100 ml of anhydrous diethyl ether and treated with anhydrous hydrogen chloride gas. The resultant precipitate was collected and treated with 500 ml of an aqueous 10% sodium carbonate solution to yield 23.5 g of (E)-(4-chlorophenyl)(cyclopropyl)methanone oxime as a solid, m.p. 101°–103° C. The nmr spectrum was consistent with the proposed structure.

C. Preparation of (E)-(4-chlorophenyl)(cyclopropyl)methanone O-[(2-methyl[1,1'-biphenyl]-3-yl)methyl]oxime In a manner similar to General Procedure F of European Patent Publication No. 4,754, published Oct. 17, 1979, 1.96 g (0.01 mole) of (E)-(4-chlorophenyl)(cyclopropyl)methanone oxime was treated with 0.23 g (0.01 mole) of sodium ethoxide in 10 ml of ethanol, and the mixture was evaporated to dryness. The residue was dissolved in a minimum amount of solvent consisting of N,N-dimethylformamide and t-butanol (9:1 ratio) and treated with 2.16 g (0.01 mole) of 3-chloromethyl-2-methyl[1,1'-biphenyl] to yield, after purification by column chromatography, 0.83 g of (E)-(4-chlorophenyl)(cyclopropyl)methanone O-[(2-methyl[1,1'-biphenyl]-3-yl)methyl]oxime as an oil.

Analysis calc'd for $C_{24}H_{22}ClNO$: C, 76.70; H, 5.86; Found: C, 75.05; H, 5.64.

NMR (CDCl$_3$) ppm: 0.5–0.95 (m, 5H); 2.10 (s, 3H); 5.15 (s, 2H); 7.08–7.42 (m, 12H).

In Examples 2–4 the EZ oxime was prepared from the appropriate ketone and hydroxylamine hydrochloride by the method of Example 1A.

In Examples 2–16 the EZ oxime mixture was converted into the E oxime by the procedure of Example 1B.

EXAMPLE 2

Synthesis of (E)-(4-chlorophenyl)(cyclopropyl)methanone O-[(2,4,6-trifluoro[1,1'-bisphenyl]-3-yl)methyl]oxime In a manner similar to Example 6 of U.S. Pat. No. 4,079,149, the reaction of 0.59 g (0.003 mole) of (E)-(4-chlorophenyl)(cyclopropyl)methanone oxime with 0.072 g (0.003 mole) of sodium hydride and 0.77 g (0.003 mole) of 3-chloromethyl-2,4,6-trifluoro[1,1'-biphenyl] in 25 ml of a 20% solution of N,N-dimethylformamide in toluene produced 0.5 g of (E)-(4-chlorophenyl)(cyclopropyl)methanone O-[(2,4,6-trifluoro[1,1'-biphenyl]-3-yl)methyl]oxime as an oil.

Analysis calc'd. for $C_{23}H_{17}ClF_3NO$: C, 66.45; H, 4.36; Found: C, 67.20; H, 4.96.

NMR (CDCl$_3$) ppm: 0.58–1.02 (m, 2H); 1.08–1.41 (m, 3H); 5.15 (s, 2H); 7.18–8.1 (m, 10H).

EXAMPLE 3

Synthesis of (E)-(4-chlorophenyl)(cyclopropyl)methanone O-[(2,6-difluoro[1,1'-biphenyl]-3-yl)methyl]oxime In a manner similar to Example 2, the reaction of 0.59 g (0.003 mole) of (E)-(4-chlorophenyl)(cyclopropyl)methanone oxime with 0.072 g (0.003 mole) of sodium hydride and 0.72 g (0.003 mole) of 3-chloromethyl-2,6-difluoro[1,1'-biphenyl] in 25 ml of a 20% solution of N,N-dimethylformamide in toluene produced (E)-(4-chlorophenyl)(cyclopropyl)methanone O-[(2,6-difluoro[1,1'-biphenyl]-3-yl)methyl]oxime as an oil.

Analysis calc'd. for $C_{25}H_{18}ClF_3NO$: C, 69.50; H, 4.81; Found: C, 68.57; H, 5.33.

NMR (CDCl$_3$) ppm: 0.77–1.03 (m, 2H); 1.18–1.37 (m, 3H); 5.15 (s, 2H); 7.22–7.44 (m, 11H).

EXAMPLE 4

Synthesis of (E)-(4-chlorophenyl)(cyclopropyl)methanone O-[(2,4-dimethyl[1,1'-biphenyl]-3-yl)methyl]oxime In a manner similar to Example 2, the reaction of 2.93 g (0.015 mole) of (E)-(4-chlorophenyl)(cyclopropyl)methanone oxime with 0.36 g (0.015 mole) of sodium hydride and 3.45 g (0.015 mole) of 3-chloro-2,4-dimethyl[1,1'-biphenyl] in 75 ml of a 20% by volume solution of N,N-dimethylformamide in toluene produced (E)-(4-chlorophenyl)(cyclopropyl)methanone O-[(2,6-dimethyl[1,1'-biphenyl]-3-yl)methyl]oxime as an oil.

Analysis calc'd. for $C_{25}H_{24}ClNO$: C, 77.01; H, 6.20; Found: C, 76.29; H, 6.30.

NMR (CDCl$_3$) ppm: 0.58–0.92 (m, 5H); 2.05–2.15 (d, 3H); 2.43–2.58 (d, 3H); 5.15 (s, 2H); 7.05–7.52 (m, 11H).

EXAMPLE 5

Synthesis of (E)-(4-t-butylphenyl)(cyclopropyl)methanone O-[(2-methyl[1,1'-biphenyl]-3-yl)methyl]oxime

A. Preparation of (E,Z)-(4-t-butylphenyl)(cyclopropyl)methanone oxime

In a manner similar to Procedure A of *J. Med. Chem.* 23, 620–624 (1980), the reaction of 5.5 g (0.0272 mole) of (4-t-butylphenyl)(cyclopropyl) ketone and 3.78 g (0.0544 mole) of hydroxylamine hydrochloride in 350 ml of pyridine produced 2.4 g of (E,Z)-(4-t-butylphenyl)(cyclopropyl)methanone oxime as a solid.

This reaction was repeated with 6.4 g of the ketone and 4.4 g of hydroxylamine hydrochloride to give an additional 3.45 g of the oxime product, which was combined with the 2.4 g produced above.

B. Preparation of (E)-(4-t-butylphenyl)(cyclopropyl)methanone oxime

In a manner similar to Example 1B, 5.45 g (0.025 mole) of (E,Z)-(4-t-butylphenyl)(cyclopropyl)methanone oxime was dissolved in 50 ml of anhydrous diethyl ether, and the resulting solution was saturated with anhydrous hydrogen chloride gas. The resultant precipitate was collected and treated with 60 ml of an aqueous 10% sodium carbonate solution to yield (E)-(4-t-butylphenyl)(cyclopropyl)methanone oxime as a solid.

The nmr spectrum was consistent with the proposed structure.

C. Preparation of (E)-(4-t-butylphenyl)(cyclopropyl)methanone O-[(2-methyl[1,1'-biphenyl]-3-yl)methyl]oxime In a manner similar to Example 2, the reaction of 0.75 g (0.0034 mole) of (E)-(4-t-butylphenyl)(cyclopropyl)methanone oxime with 0.2 g (0.008 mole) of sodium hydride and 0.74 g (0.0034 mole) of 3-chloromethyl-2-methyl[1,1'-biphenyl] in 25 ml of a 20% solution of N,N-dimethylformamide in toluene produced (E)-(4-t-butylphenyl)(cyclopropyl)methanone O-[(2-methyl[1,1'-biphenyl]-3-yl)methyl]oxime as an oil.

Analysis calc'd. for $C_{28}H_{31}NO$: C, 84.81; H, 7.63; N, 3.53; Found: C, 84.35; H, 8.22; N, 3.04.

NMR (CDCl$_3$) ppm: 0.62–0.94 (m, 5H); 1.10 (s, 9H); 2.10 (s, 3H); 5.25 (s, 2H); 7.15–7.45 (m, 12H).

In Examples 6–16 the EZ-oxime was prepared from the appropriate ketone and hydroxylamine hydrochloride by the method of Example 5A, and the coupling reaction of the E oxime and substituted-biphenylmethyl halide was conducted by the method of Example 2.

EXAMPLE 6

(E)-(4-ethylphenyl)(cyclopropyl)methanone O-[(2-methyl[1,1'-biphenyl]-3-yl)methyl]oxime Analysis calc'd. for $C_{26}H_{27}NO$: C, 84.51; H, 7.37; N, 3.79; Found: C, 84.60; H, 7.67; N, 3.82.

NMR (CDCl$_3$) ppm: 0.62–0.93 (m, 5H); 1.08–1.36 (t, 3H); 2.10 (s, 3H); 2.25–2.58 (q, 2H); 5.25 (s, 2H); 7.18–7.44 (m, 12H).

EXAMPLE 7

(E)-(4-isopropylphenyl)(cyclopropyl)methanone O-[(2-methyl[1,1'-biphenyl]-3-yl)methyl]oxime Analysis calc'd for $C_{27}H_{29}NO$: C, 84.55; H, 7.62; N, 3.65; Found: C, 84.30; H, 7.35; N, 3.38.

NMR (CDCl$_3$) ppm: 0.65–0.95 (m, 5H); 1.18–1.36 (d, 7H); 2.15 (s, 3H); 5.15 (s, 2H); 7.1–7.44 (m, 12H).

EXAMPLE 8

(E)-(phenyl)(cyclopropyl)methanone O-[(2-methyl[1,1'-biphenyl]-3-yl)methyl]oxime Analysis calc'd for $C_{24}H_{23}NO$: C, 84.42; H, 6.78; N, 4.10; Found: C, 81.73; H, 6.75; N, 3.91.

NMR (CDCl$_3$) ppm: 0.62–1.05 (m, 5H); 2.15 (s, 3H); 5.18 (s, 2H); 7.18–7.52 (m, 13H).

EXAMPLE 9

(E)-(4-trifluoromethylphenyl)(cyclopropyl)methanone O-[(2-methyl[1,1'-biphenyl]-3-yl)methyl]oxime NMR (CDCl$_3$) ppm: 0.5–0.92 (m, 5H); 2.1 (s, 3H); 5.1 (s, 2H); 7.0–7.46 (m, 12H).

EXAMPLE 10

(E)-(4-trifluoromethoxyphenyl)(cyclopropyl)methanone O-[(2-methyl[1,1'-biphenyl]-3-yl)methyl]oxime NMR (CDCl$_3$) ppm: 0.7–1.1 (m, 5H); 2.25 (s, 3H); 5.35 (s, 2H); 7.15–7.5 (m, 12H).

EXAMPLE 11

(E)-(2,4-dimethylphenyl)(cyclopropyl)methanone O-[(2-methyl[1,1'-biphenyl]-3-yl)methyl]oxime Analysis calc'd for $C_{26}H_{27}NO$: C, 84.28; H, 7.62; N, 3.78; Found: C, 78.00; H, 8.10; N, 7.75.

EXAMPLE 12

(E)-(2,4-dichlorophenyl)(cyclopropyl)methanone O-[(2-methyl[1,1'-biphenyl]-3-yl)methyl]oxime Analysis calc'd for $C_{24}H_{21}Cl_2NO$: C, 70.24; H, 5.17; N, 3.14; Found: C, 75.39; H, 5.39; N, 2.94.

NMR (CDCl$_3$) ppm: 1.1–1.18 (m, 5H); 2.15 (s, 3H); 5.15–5.35 (t, 2H); 7.15–7.65 (m, 11H).

EXAMPLE 13

(E)-(4-fluorophenyl)(cyclopropyl)methanone O-[(2-methyl[1,1'-biphenyl]-3-yl)methyl]oxime Analysis calc'd for $C_{24}H_{22}FNO$: C, 80.19; H, 6.16; N, 3.89; Found: C, 71.77; H, 5.28; N, 2.82.

NMR (CDCl$_3$) ppm: 0.58–1.02 (m, 5H); 2.08 (s, 3H); 5.15 (s, 2H); 6.95–7.58 (m, 12H).

EXAMPLE 14

(E)-1-(4-chlorophenyl)-2-(cyclopropyl)ethanone O-[(2-methyl[1,1'-biphenyl]-3-yl)methyl]oxime Analysis calc'd for $C_{25}H_{24}ClNO$: C, 77.00; H, 6.22; N, 3.59; Found: C, 78.18; H, 7.20; N, 2.81.

NMR (CDCl$_3$) ppm: 0.78–0.98 (m, 5H); 2.15 (s, 3H); 2.7–3.05 (d, 2H); 5.15 (s, 2H); 7.18–7.68 (m, 12H).

EXAMPLE 15

(E)-(4-chlorophenyl)(cyclobutyl)methanone O-[2-methyl[1,1'-biphenyl[-3-yl)methyl]oxime Analysis calc'd for $C_{25}H_{24}FNO$: C, 80.40; H, 6.47; N, 3.75; Found: C, 79.12; H, 6.20; N, 3.94.

NMR (CDCl$_3$) ppm: 0.78–0.95 (m, 7H); 2.05–2.22 (d, 3H); 5.15–5.3 (d, 2H); 6.95–7.48 (m, 12H).

EXAMPLE 16

(E)-(4-chlorophenyl)-2-methyl-1-propanone O-[(2-methyl[1,1'-biphenyl]-3-yl)methyl]oxime Analysis calc'd for $C_{24}H_{24}ClNO$: C, 76.27; H, 6.40; Found: C, 76.65; H, 6.11.

NMR (CDCl$_3$) ppm: 0.98–1.25 (m, 6H); 2.10 (s, 3H); 5.10 (s, 2H); 7.18–7.43 (m, 13H).

EXAMPLE 17

Synthesis of (E)-(4-difluoromethoxyphenyl)(cyclopropyl)methanone O-[(2-methyl[1,1'-biphenyl]-3-yl)methyl]oxime

A. Preparation of 4-(difluoromethoxy)benzonitrile

Under a dry argon atmosphere a mixture of 10.0 g (0.084 mole) of 4-cyanophenol, 33.6 g (0.84 mole) of sodium hydroxide, 110 ml of water, and 130 ml of tetrahydrofuran was stirred in a Morton flask and heated at reflux. During 1.25 hour, 8.6 g (0.99 mole) of chlorodifluoromethane was added to the reaction mixture. After complete addition, the mixture was allowed to cool to room temperature and was stirred for approximately 18 hours. The reaction mixture was poured into 500 g of ice water, the resulting mixture filtered, and the filtrate extracted with three 300 ml portions of diethyl ether. The ether extracts were combined, dried over anhydrous potassium carbonate, and filtered. The filtrate was evaporated under reduced pressure to give an oil which crystallized upon standing. The product was recrystallized from toluene/methylcyclohexane to give 5.2 g of 4-difluoromethoxybenzonitrile as a white solid, m.p. 36°–37° C.

B. Preparation of (4-difluoromethoxyphenyl)(cyclopropyl) ketone

Upon a dry argon atmosphere, a mixture of 1.6 g (0.066 mole) of magnesium, 7.9 g (0.066 mole) of cyclopropylbromide, 60 ml of anhydrous diethyl ether, and 60 ml of anhydrous tetrahydrofuran was heated at reflux for 2.5 hours. The stirred mixture was cooled to room temperature, and a solution of 11.1 g (0.066 mole) of (4-difluoromethoxybenzonitrile) in 40 ml of anhydrous diethyl ether and 40 ml of anhydrous tetrahydrofuran was added during one hour. After complete addition, the mixture was heated at reflux for two hours, then stirred at room temperature for approximately 18 hours. A 100 ml portion of 2 N hydrochloric acid was added slowly to the mixture, and the whole was stirred for one hour. The mixture was extracted with three 100 ml portions of diethyl ether. The ether extracts were combined, dried over anhydrous magnesium sulfate and filtered. The filtrate was evaporated under reduced pressure to give an oil. The oil was subjected to column chromatography on silica gel, eluting with toluene-/ethyl acetate (95:5), to give 8.3 g of (4-difluoromethoxyphenyl)(cyclopropyl) ketone.

C. Preparation of (E)-(4-difluoromethoxyphenyl)(cyclopropyl)methanone oxime

A stirred mixture of 7.8 g (0.037 mole) of (4-difluoromethoxyphenyl)(cyclopropyl) ketone, 2.6 g (0.037 mole) of hydroxylamine hydrochloride, and 50 ml of pyridine in 50 ml of ethanol was heated at reflux for approximately 18 hours. The reaction mixture was evaporated under reduced pressure to give a liquid residue. The residue was dissolved in methylene chloride and washed with 200 ml of a saturated aqueous solution of sodium chloride. The organic phase was dried over anhydrous magnesium sulfate, filtered, and the filtrate evaporated under reduced pressure to give an oil. The oil was diluted with 30 ml of toluene and 250 ml of n-heptane, and the solution placed in a freezer. A solid separated from the toluene/n-heptane solution and was collected by filtration. The solid was recrystallized from methylcyclohexane to give 3.0 g of (E)-(4-difluoromethoxyphenyl)(cyclopropyl)methanone, m.p. 110.5°–111° C. The toluene/n-heptane mother liquor was evaporated under reduced pressure to leave 3.1 g of an oil. The oil was found by NMR and IR analysis to be the corresponding (Z) isomer.

D. Preparation of (E)-(4-difluoromethoxyphenyl)(cyclopropyl)methanone O-[(2-methyl[1,1'-biphenyl]-3-yl)methyl]oxime Under a dry argon atmosphere a solution of 1.0 g (0.0044 mole) of (E)-(4-difluoromethoxyphenyl)(cyclopropyl)methanone oxime in 50 ml of dry tetrahydrofuran was added to a stirred solution of 0.95 g (0.0044 mole) of 3-chloromethyl-2-methyl [1,1'-biphenyl], 0.29 g (0.0044 mole) of powdered potassium hydroxide, and 0.14 g (0.00044 mole) of tetrabutylammonium bromide in 45 ml of dry tetrahydrofuran. The reaction mixture was stirred at room temperature for approximately 18 hours then evaporated under reduced pressure to give a liquid. The liquid was diluted with methylene chloride, and the mixture washed with water. The aqueous wash was extracted with methylene chloride. The organic phases were combined, dried over anhydrous magnesium sulfate, and filtered. The filtrate was evaporated under reduced pressure to give an oil. The oil was subjected to column chromatography on silica gel, eluting with toluene to give 1.73 g of (E)-(4-difluoromethoxyphenyl)(cyclopropyl)methanone O-[(2-methyl[1,1'-biphenyl]-3-yl)methyl]oxime as an oil.

Analysis calc'd for $C_{25}H_{23}F_2NO_2$: C 73.64; H 5.68; Found: C 74.72; H 5.98.

NMR (CDCl$_3$) ppm: 0.57–1.30(m,4H); 2.03–2.43(m,1H); 2.27(s,3H); 5.30(s,2H); 6.50(t,1H); 7.02–7.57(m,12H).

EXAMPLE 18

Synthesis of (E)-(4-diflouromethoxyphenyl)(cyclopropyl)methanone O-[(2,4,5,6-tetrafluoro[1,1'-biphenyl]-3-yl)methyl]oxime This compound was prepared in a manner similar to the procedure described in Example 17.

Analysis calc'd for $C_{24}H_{17}F_6NO_2$: C 61.44; H 3.68; Found: C 63.33; H 4.23.

NMR (CDCl$_3$) ppm: 0.53–1.30(m,4H); 1.97–2.40(m,7H); 5.30(m,2H); 6.50(t,1H); 6.83–7.53(m,9H).

In the method aspect of this invention, an effective insecticidal or acaricidal amount of the compound of formula I is applied to the locus where control is desired, i.e., to the insect or acarid itself or to the foliage or seeds of agricultural plants. The compounds are useful for the control of household, veterinary, and crop pests of the phylum Arthropoda, and may be applied as technical material or as formulated product. Typical formulations include compositions of the active ingredient in combination with an agriculturally acceptable carrier or extender, preferably with a surface active agent, and optionally with other active ingredient(s). Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of active ingredient depending upon the particular agent used, the additives and carriers used, other active ingredients, and the desired mode of application. With due consideration to these factors the active ingredient of a typical formulation may, for example, be suitably present at a concentration of about 0.01% up to about 99.5%, preferably 0.1% up to 90% or 95%, of the formulation. An agriculturally acceptable carrier may comprise about 99.5% by weight to as low as about 0.5% by weight of the formulation. Compatible surface active agents, if employed in a formulation, may be present at various concentrations, suitably in the range of 1 to 30% by weight of the formulation.

The formulation may be used as such or diluted to a desired use dilution with a diluent or carrier suitable for facilitating dispersion of the active ingredients. A concentration of the active ingredient in the use dilution may be in the range of 0.001% to about 50%, preferably up to about 10% by weight.

Many variations of spraying, dusting, and controlled or slow release compositions of a type known in the art may be used by substituting or adding an insecticidal compound or compounds of this invention into the compositions known or apparent to the art.

The insecticidal or acaricidal compounds of this invention may be formulated and applied with other compatible active agents including nematicides, insecticides, acaricides, fungicides, plant regulators, herbicides, fertilizers, and the like.

In applying these compounds, whether alone or with other agricultural chemicals, an effective insecticidal or acaricidal amount of the active ingredient must be applied. While the application rate will vary widely depending on the choice of compound, formulation, mode of application, plant species being protected, planting density and other like factors, a suitable use rate for agricultural crops may be in the range of 0.01 to 3 k/ha, preferably 0.05 to about 1 k/ha.

The oxime ethers of this invention were tested for insecticidal/acaricidal activity as described in Example 19 below.

EXAMPLE 19

Insecticidal/Acaricidal Activity

Insecticidal or acaricidal activity was determined in a series of tests including a foliar application test, a soil drench test for determining upward systemic activity, a topical application test, and a soil incorporated test for residual activity against corn rootworm.

Foliar Application Test

The compounds were tested for insecticidal/acaricidal activity on green plant foliage according to the following procedure: Test solutions containing 500, 64, and 16 ppm of test compound were prepared. The 500 ppm test solutions were made by mixing 19 ml of water with 1 ml of a 1% w/v stock solution of test compound in acetone, the 1% stock solution also containing 0.5 drop of octylphenoxypolyethoxyethanol surfactant for each ml of acetone present. The 64 ppm test solutions were prepared by dissolving 37 mg of test compound in 250 ml of an acetone-water-surfactant stock solution (1:9 acetone-water, one drop of octylphenoxypolyethoxyethanol surfactant for each 100 ml of acetone-water) to give a solution containing 146 ppm of test compound, then mixing 22 ml of the 146 ppm solution with 28 ml of the acetone-water-surfactant stock solution to give 50 ml of a 64 ppm test solution. The 16 ppm test solution was obtained by dilution of the 64 ppm solution with additional acetone-water-surfactant stock solution.

The insect/acarid test species used were cabbage looper (*Trichoplusia ni* [Hubner]), Mexican bean beetle (*Epilachna varivestis* Muls.), southern armyworm (*Spodoptera eridania* [Cram.]), pea aphid (*Acyrthosiphon pisum* [Harris]), and twospotted spider mite (*Tetranychus urticae* [Koch]).

The activity against Mexican bean beetle, southern armyworm, and cabbage looper was determined by spraying the upper and lower surfaces of the leaves of pinto bean plants with test solution until run-off, and infesting with 3rd instar larvae (ten larvae for each of two replicates for each compound) after the foliage had dried.

The activity against pea aphids was determined in similar fashion, except that broad bean plants were used and the leaves were infested with adult aphids.

The activity against mites was determined on pinto bean plants the leaves of which were infested with adult mites (about 75 mites for each of two replicates for each compound) then sprayed until run-off with test solution.

The pinto bean plants were infested by placing sections of leaves from earlier infested plants onto the leaves of the test plants.

To prevent escape of the insects from the test site, the test plant or the incised leaves were placed in capped paper cups or other containers. The tests were transferred to a holding room at 80° C. and 50% relative humidity for an exposure period of 48 hours. At the end of this time the dead and living insects/mites were counted and the percent mortality was calculated.

Several oxime ethers in the prior art were also tested for insecticidal/acaricidal activity by this procedure. The structures of the compounds tested are shown in table 1, and the testing results are given in comparison form in table 2. In almost every comparison the compounds of the invention were more active overall than the prior art compounds.

Soil Drench Systemic Test

The present compounds were tested as 146 ppm test solutions for upward systemic insecticidal activity. The insect species used was the pea aphid.

Broad bean seedlings that have reached a height of 5-6 cm were transplanted from germination flats into a soil of three parts sand and one part peat moss contained in 7.6 cm plastic pots. The transplanted plants were allowed a two-day recovery period to insure that the test compound does not enter the plants via damaged roots. Before application of the test compound the soil of the test plants was moistened, but not saturated, with water. The pots of the test plants were placed in a 9 cm petrie plate lid, and a 25 ml portion of a solution containing 146 ppm (wt/v-8 kg/ha) of the test compound was poured evenly over the soil surface of each of the test plants, being careful not to wet the foliage or stems. The 146 ppm test solution was prepared by dissolving 37 mg of the test compound in 250 ml of a stock solution of 10% acetone-water containing one drop of octylphenoxypolyethoxyethanol for each 100 ml of stock solution. The test compound was allowed a three-day translocation period after which the plants were infested with adult aphids (ten aphids for each of two replicates for each compound). The test plants were then kept at 80° C. and 50% relative humidity for an exposure period of 48 hours. At the end of this time the dead and living aphids were counted and the percent mortality was calculated.

The results of these tests are shown in Table 2 below in the column under the heading "PA(SD)". For comparison, data are also given in Table 2 for several prior art oxime ethers which also were tested for systemic activity by this procedure. Many of the present compounds were active in this test whereas none of the prior art test compounds were active.

Topical Application Test

In this test a solution of the test compound in acetone is applied topically to the test insects. The insect species employed were Mexican bean beetle (*Epilachna varivestis* Muls.), milkweed bug (*Oncopeltus faciatus* [Dallas]), southern armyworm (*Spodoptera eridania* [Cram.]), southern corn rootworm (*Diabrotica undecimpunctata* Howardi), cabbage looper (*Trichoplusia ni* [Hubner]), and tobacco budworm (*Heliothis virescens* [Fabricius]).

Two replicates of ten larvae of each test insect species were employed for each test compound. A 9 cm petri dish lined with a piece of filter paper, and containing a food source was employed for each replicate. A one microliter droplet of a solution of test compound in acetone was applied to the second or third dorsal thoracic segment of each larva. A series of concentrations ranging from 5.0 mg/ml (5000 ng/$\mu$l) to 0.200 mg/ml (200 ng/$\mu$l) of test compound was used. Mortality data were collected 24 hours after application of the test solution.

The results of this test are given in table 3 below. Data are also presented for comparison purposes for several prior art oxime ethers. In almost every comparison the present compounds were more active overall than the prior art compounds.

Soil Residual Test

Compounds of the invention showing good activity against southern corn rootworm by topical application were tested for residual activity against the rootworm in a soil environment, at testing rates of 10, 4, 2, and 0.5 ppm in soil, and for residual periods of 14, 21, and 42 days. Only compounds giving 70% or greater activity after 14 days at 10 ppm were tested at the lower concentration rates.

For a testing rate of 10 ppm, 15 mg of test compound was dissolved in 100 ml of an acetone-water-surfactant stock solution (1:9 acetone-water, one drop of octylphenoxypolyethoxyethanol surfactant for each 100 ml of acetone-water) to give a stock solution containing 150 ppm of test compound, and 2 ml of the 150 ppm stock solution was thoroughly mixed with 30 ml of air-dried topsoil in a 120 ml plastic cup to give a concentration of test compound in the soil of 10 ppm. For a testing rate of 4 ppm, 2 ml of a 60 ppm stock solution of test compound in acetone-water-surfactant was admixed with 30 ml of air-dried topsoil in a plastic cup. Similarly, 2 ml of a 30 ppm test compound stock solution mixed with 30 ml of air-dried soil gave a testing rate of 2 ppm, and 2 ml of a 7.5 ppm test compound stock solution mixed with 30 ml of dry topsoil gave a testing rate of 0.5 ppm.

Each cup of treated topsoil was capped with a plastic lid and stored for 14, 21, or 42 days. On the terminal day of the storage period, the cups were infested with southern corn rootworm larvae (10 specimens for each of two replicates for each test compound), and a kernel of germinating corn was added to each cup as a food supply. The cups were recapped and returned to storage for 3 days. At the end of this time the dead and living rootworms were counted and the percent mortality was calculated.

The results of this test are given in table 4. The compound of Example 10, which contains a trifluoromethoxy group at C-4 of the phenyl ring of the ketoxime portion of the molecule, was far superior to the other compounds, many of which were inactive or showed only low activity in the test.

Comparison data are also given in table 4 for three prior art oxime ethers. Two of the prior art compounds were inactive in this test and the third was only slightly active.

In the tables which follow, the prior art compounds used as standards for comparison are identified by the letters A-G, and the compounds of the invention by the numbers 1-16. All the compounds tested were E isomers. The chemical identities of the compounds are given in Table 1 below.

TABLE 1

Chemical Identities

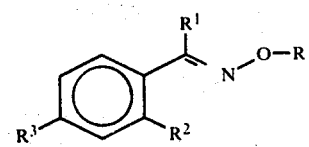

| Cpd. | Isomer | R$^1$ | R$^2$ | R$^3$ | R |
|---|---|---|---|---|---|
| A | E | ◁ | —H | —Cl | 3-PB |
| 1 | " | " | " | " | 2-M[BP]M |
| 2 | " | " | " | " | 2,4,6-F$_3$[BP]M |
| 3 | " | " | " | " | 2,6-F$_2$[BP]M |
| 4 | " | " | " | " | 2,4-M$_2$[BP]M |
| B | " | " | " | —H | 3-PB |
| 8 | " | " | " | " | 2-M[BP]M |
| 6 | " | " | " | —C$_2$H$_5$ | " |
| 7 | " | " | " | ─< | " |
| 5 | " | " | " | ─+ | " |
| 9 | " | " | " | —CF$_3$ | " |
| 10 | " | " | " | —OCF$_3$ | " |
| 17 | " | " | " | —OCHF$_2$ | " |
| 18 | " | " | " | " | 2,4,5,6-F$_4$[BP]M |
| 11 | " | " | —CH$_3$ | —CH$_3$ | 2-M[BP]M |
| C | " | " | —Cl | —Cl | 3-PB |
| 12 | " | " | " | " | 2-M[BP]M |
| D | " | " | —H | —F | 3-PB |
| 13 | " | " | " | " | 2-M[BP]M |
| E | " | ◁ | " | —Cl | 3-PB |
| 14 | " | " | " | " | 2-M[BP]M |
| F | " | ◇ | " | —F | 3-PB |
| 15 | " | " | " | " | 2-M[BP]M |
| G | " | ─< | " | —Cl | 3-PB |

TABLE 1-continued
Chemical Identities $$\underset{R^3}{\underset{|}{\bigcirc}}\overset{R^1}{\underset{R^2}{\bigcirc}}\text{C}=\text{N}-\text{O}-\text{R}$$

| Cpd. | Isomer | R¹ | R² | R³ | R |
|------|--------|-----|-----|-----|---|
| 16 | " | " | " | " | 2-M[BP]M |

3-PB is —CH₂—(phenyl)—O—(phenyl)

2-M[BP]M is —CH₂—(phenyl with CH₃)—(phenyl)

2,4,6-F₃[BP]M is —CH₂—(phenyl with F,F,F)—(phenyl)

2,6-F₂[BP]M is —CH₂—(phenyl with F,F)—(phenyl)

2,4-M₂[BP]M is —CH₂—(phenyl with CH₃,CH₃)—(phenyl)

2,4,5,6-F₄[BP]M is —CH₂—(phenyl with F,F,F,F)—(phenyl)

TABLE 2
Comparative Foliar Activity

| Compound | Rate (ppm) | CL | MBB | SAW | PA | PA(SD) | TSM |
|----------|-----------|-----|-----|-----|-----|--------|-----|
| A | 500 | — | — | 100 | 100 | — | 0 |
|   | 146 | — | — | — | — | 0 | — |
|   | 64 | — | 35 | 100 | 35 | — | — |
|   | 16 | — | 0 | 80 | 0 | — | — |
| 1 | 500 | — | — | 100 | 100 | — | 85 |
|   | 146 | — | — | — | — | 100 | — |
|   | 64 | — | 100 | 100 | 100 | — | — |
|   | 16 | — | 100 | 100 | 90 | — | — |
| 2 | 500 | — | — | 100 | 100 | — | 0 |
|   | 146 | — | — | — | — | — | — |
|   | 64 | 100 | 60 | — | — | — | — |
|   | 16 | 50 | 35 | — | — | — | — |
| 3 | 500 | — | — | 100 | 90 | — | 0 |
|   | 146 | — | — | — | — | — | — |
|   | 64 | 80 | 100 | — | — | — | — |
|   | 16 | 55 | 50 | — | — | — | — |
| 4 | 500 | — | — | 100 | 100 | — | 100 |
|   | 146 | — | — | — | — | 0 | — |
|   | 64 | 85 | 95 | — | 85 | — | — |
|   | 16 | 65 | 65 | — | 65 | — | — |
| B | 1250 | — | — | — | 95 | — | 0 |
|   | 146 | — | — | — | — | 0 | — |
|   | 64 | 0 | 20 | — | 0 | — | — |
|   | 16 | 0 | 0 | — | 0 | — | — |
| 8 | 1250 | — | — | 100 | 100 | — | 100 |
|   | 146 | — | — | — | — | 0 | — |
|   | 64 | 70 | 95 | — | 25 | — | — |
|   | 16 | 25 | 30 | — | 0 | — | — |
| 6 | 1250 | — | — | 100 | 100 | — | 100 |
|   | 146 | — | — | — | — | 70 | — |
|   | 64 | 100 | 100 | — | 85 | — | — |
|   | 16 | 90 | 95 | — | 65 | — | — |
| 7 | 1250 | — | — | 100 | 100 | — | 0 |
|   | 146 | — | — | — | — | 90 | — |
|   | 64 | 100 | 100 | — | 80 | — | — |
|   | 16 | 90 | 90 | — | 60 | — | — |
| 5 | 1250 | — | — | 100 | 100 | — | 100 |
|   | 146 | — | — | — | — | 45 | — |
|   | 64 | 100 | 100 | — | 85 | — | — |
|   | 16 | 75 | 100 | — | 55 | — | — |
| 9 | 1250 | — | — | 100 | 100 | — | 100 |
|   | 146 | — | — | — | — | 30 | — |
|   | 64 | 100 | 100 | — | 90 | — | 98 |
|   | 16 | 100 | 100 | — | 70 | — | 72 |
| 10 | 1250 | — | — | 100 | 100 | — | 100 |
|    | 146 | — | — | — | — | 100 | — |
|    | 64 | 100 | 90 | — | 100 | — | 100 |
|    | 16 | 100 | 90 | — | 100 | — | 100 |
| 17 | 1000 | — | 100 | 100 | — | — | 100 |
|    | 146 | — | — | — | — | — | — |
|    | 64 | — | 100* | 100* | — | — | 100* |
|    | 16 | — | 90* | 93* | — | — | 95* |
| 18 | 64 | — | 35 | 100 | — | — | 20 |
|    | 16 | — | 0 | 85 | — | — | 0 |
| 11 | 1250 | — | — | 100 | 100 | — | 0 |
|    | 146 | — | — | — | — | 15 | — |
|    | 64 | 100 | 100 | — | 90 | — | — |
|    | 16 | 45 | 50 | — | 15 | — | — |
| C | 1250 | — | — | 100 | 100 | — | 0 |
|   | 146 | — | — | — | — | 0 | — |
|   | 64 | 60 | 90 | — | 0 | — | — |
|   | 16 | 0 | 0 | — | 0 | — | — |
| 12 | 1250 | — | — | 100 | 100 | — | 100 |
|    | 146 | — | — | — | — | 0 | — |
|    | 64 | 65 | 50 | — | 20 | — | — |
|    | 16 | 20 | 0 | — | 0 | — | — |
| D | 1250 | — | — | 100 | 100 | — | 0 |
|   | 146 | — | — | — | — | 0 | — |
|   | 64 | 75 | 70 | — | 0 | — | — |
|   | 16 | 30 | 10 | — | 0 | — | — |
| 13 | 1250 | — | — | 100 | 100 | — | 100 |
|    | 146 | — | — | — | — | 50 | — |
|    | 64 | 100 | 90 | — | 20 | — | — |
|    | 16 | 70 | 55 | — | 0 | — | — |
| E | 1250 | — | — | 100 | 100 | — | 100 |
|   | 146 | — | — | — | — | 0 | — |
|   | 64 | 75 | 30 | — | 0 | — | — |
|   | 16 | 0 | 10 | — | 0 | — | — |
| 14 | 1250 | — | — | 100 | 100 | — | 0 |
|    | 146 | — | — | — | — | 0 | — |
|    | 64 | 20 | 95 | — | 25 | — | — |
|    | 16 | 0 | 20 | — | 0 | — | — |
| F | 1250 | — | — | 25 | 0 | — | 0 |
| 15 | 1250 | — | — | 100 | 100 | — | 100 |
| G | 500 | — | — | 100 | — | — | 0 |
|   | 146 | — | — | — | — | 0 | — |
|   | 64 | — | 20 | 85 | 0 | — | — |
|   | 16 | — | 5 | 0 | 0 | — | — |
| 16 | 500 | — | — | 100 | — | — | 75 |
|    | 146 | — | — | — | — | 0 | — |
|    | 64 | — | 45 | 100 | 95 | — | — |
|    | 16 | — | 15 | 0 | 60 | — | — |

*Average of two tests (Compound 17)
CL: Cabbage looper
MBB: Mexican bean beetle
SAW: Southern armyworm
PA: Pea aphid
PA(SD): Pea aphid (soil drench)
TSM: Two-spotted spider mite

TABLE 3

Comparative Topical Activity

| Cmpd. | Rate (ng/insect) | MBB | MWB | SAW | SCR | CL | TBW |
|---|---|---|---|---|---|---|---|
| A | 5000 | 0 | 100 | 100 | — | — | — |
| 1 | 5000 | 100 | 100 | 100 | — | — | — |
| 2 | 5000 | 55 | 90 | 60 | — | — | — |
| 3 | 5000 | 75 | 90 | 65 | — | — | — |
| 4 | 5000 | 100 | 100 | 100 | — | — | — |
| B | 2500 | 50 | — | 75 | — | — | — |
|   | 1000 | — | — | — | — | 0 | — |
| 8 | 2500 | 100 | 100 | 100 | — | 0 | — |
|   | 1000 | — | — | — | — | 0 | 90 |
| 6 | 2500 | 100 | 100 | 100 | — | — | — |
|   | 1000 | — | 100 | — | — | 100 | 60 |
| 7 | 2500 | 100 | 100 | 100 | — | — | — |
|   | 1000 | — | 100 | — | — | 100 | 20 |
| 5 | 2500 | 100 | 100 | 100 | — | — | — |
|   | 1000 | — | 90 | — | — | 40 | 10 |
| 9 | 2500 | 100 | 100 | 100 | — | — | — |
|   | 1000 | — | — | — | — | 100 | 100 |
| 10 | 2500 | 100 | 95 | 100 | — | — | — |
|   | 1000 | — | — | — | — | 100 | 100 |
| 11 | 2500 | 100 | 100 | 100 | — | — | — |
|   | 1000 | — | 100 | — | — | 0 | 0 |
| C | 2500 | 65 | 0 | 100 | — | — | — |
|   | 1000 | — | — | — | — | 0 | 0 |
|   | 500 | — | — | — | 0 | — | — |
|   | 200 | — | — | 0 | — | — | — |
| 12 | 2500 | 85 | 45 | 100 | — | 0 | — |
|   | 1000 | — | — | — | — | 0 | 0 |
|   | 500 | — | — | — | 50 | — | — |
|   | 200 | 30 | — | 0 | — | — | — |
| D | 2500 | 100 | 45 | 100 | — | — | — |
|   | 1000 | — | — | — | — | 50 | 100 |
|   | 500 | — | — | — | 100 | — | — |
|   | 200 | 10 | — | 40 | — | — | — |
| 13 | 2500 | 100 | 100 | 100 | — | — | — |
|   | 1000 | — | — | — | — | 100 | 100 |
|   | 500 | — | — | — | 100 | — | — |
|   | 200 | 100 | — | 95 | — | — | — |
| E | 2500 | 90 | 80 | 100 | — | — | — |
|   | 1000 | — | — | — | — | 0 | 0 |
|   | 500 | — | — | — | 65 | — | — |
|   | 200 | 0 | — | 0 | — | — | — |
| 14 | 2500 | 90 | 90 | 100 | — | — | — |
|   | 1000 | — | — | — | — | 0 | 0 |
|   | 500 | — | — | — | 60 | — | — |
|   | 200 | 20 | — | 0 | — | — | — |
| F | 2500 | 0 | 0 | 0 | — | — | — |
|   | 500 | — | — | — | 0 | — | — |
| 15 | 2500 | 100 | 100 | 100 | — | — | — |
|   | 500 | — | — | — | 90 | — | — |
| G | 5000 | 100 | 60 | 100 | — | — | — |
| 16 | 5000 | 100 | 95 | 100 | — | — | — |

MBB: Mexican bean beetle
MWB: Milkweed bug
SAW: Southern armyworm
SCR: Southern corn rootworm
CL: Cabbage looper
TBW: Tobacco budworm

TABLE 4

Soil-Residual Activity

| Compound | Rate (ppm) | % Mortality Against Southern Corn Rootworm | | |
|---|---|---|---|---|
|   |   | 14-day | 21-day | 42-day |
| 1 | 10 | — | 5 | — |
| 2 | 10 | 0 | — | — |
| 3 | 10 | 0 | — | — |
| 4 | 10 | 45 | — | — |
| 12 | 10 | 40 | — | — |
| 15 | 10 | 15 | — | — |
| B | 10 | 0 | — | — |
| 5 | 10 | 0 | — | — |
| 6 | 10 | 0 | — | — |
| 7 | 10 | 0 | — | — |
| 8 | 10 | — | 10 | — |
| 9 | 10 | 10 | — | — |
| 10 | 10 | 70 | — | — |
| 4 | — | — | 80 | 70 |
| 2 | — | — | 30 | 50 |
| 0.5 | — | — | 25 | 20 |
| 11 | 10 | 0 | — | — |
| D | 10 | 30 | — | — |
| 13 | 10 | 60 | 30 | — |
| E | 10 | 0 | — | — |
| 14 | 10 | 0 | — | — |

We claim:

1. The E isomer of a compound of the formula

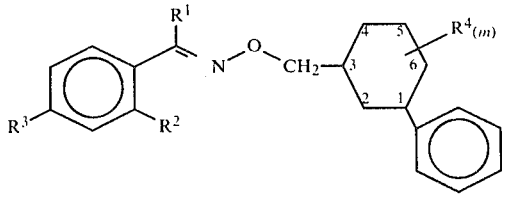

wherein $R^1$ is isopropyl, cyclopropyl, cyclopropylmethyl, or cyclobutyl; $R^2$ is hydrogen, halogen, or alkyl of 1 to 4 carbon atoms; $R^3$ is hydrogen, halogen, straight or branched chain alkyl of 1 to 4 carbon atoms, haloalkyl of 1 or 2 carbon atoms, or the group $-OCFZ^1Z^2$ wherein $Z^1$ and $Z^2$ are independently hydrogen or fluorine; and $R^4$ is alkyl of 1 to 4 carbon atoms and m is 1 or 2, or $R^4$ is halogen and m is 2–4; with the proviso that when $R^1$ is isopropyl, then m is 1 and $R^4$ is alkyl and is positioned at the C-2 carbon atom.

2. The compound of claim 1 wherein $R^1$ is isopropyl, cyclopropyl or cyclobutyl, and haloalkyl is fluoroalkyl.

3. The compound of claim 2 wherein $R^2$ is hydrogen, chlorine, or methyl; fluoroalkyl is trifluoromethyl; and one of $Z^1$ and $Z^2$ is fluorine and the other is hydrogen or fluorine.

4. The compound of claim 3 wherein m is 1 or 2 and $R^4$ is methyl and is positioned at the C-2 or C-2 and C-4 carbon atoms.

5. The compound of claim 4 wherein each of $R^2$ and $R^3$ is hydrogen or chlorine, or $R^2$ is hydrogen and $R^3$ is chlorine, fluorine, straight or branched chain alkyl of 1 to 4 carbon atoms, trifluoromethyl, difluoromethoxy, or trifluoromethoxy.

6. The compound of claim 5 wherein $R^1$ is isopropyl or cyclopropyl; $R^2$ is hydrogen, $R^3$ is chlorine, fluorine, straight or branched chain alkyl of 1 to 3 carbon atoms, trifluoromethyl, difluoromethoxy, or trifluoromethoxy, and m is 1.

7. An insecticidal/acaricidal composition comprising an insecticidally/acaricidally effective amount of the compound of any one of claims 1 to 6 in admixture with a compatible extender or carrier.

8. A method for controlling insects/acarids which comprises applying to the insect/acarid or to a locus where control is desired an insecticidally/acaricidally effective amount of the compound of any one of claims 1 to 6.

9. A method for controlling insects/acarids which comprises applying to the insect/acarid or to a locus where control is desired an insecticidally/acaricidally effective amount of the composition of claim 7.

* * * * *

UNITED STATES PATENT AND TRADEMARK OFFICE
CERTIFICATE OF CORRECTION

PATENT NO. : 4,434,182

DATED : February 28, 1984

INVENTOR(S) : Philip A. Cruickshank and Thomas G. Cullen

It is certified that error appears in the above—identified patent and that said Letters Patent is hereby corrected as shown below:

Cover page, ABSTRACT, formula should read as follows:

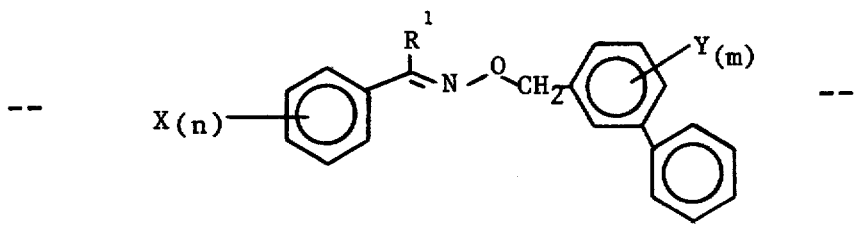

Column 20, under Claim 1, formula should read as follows:

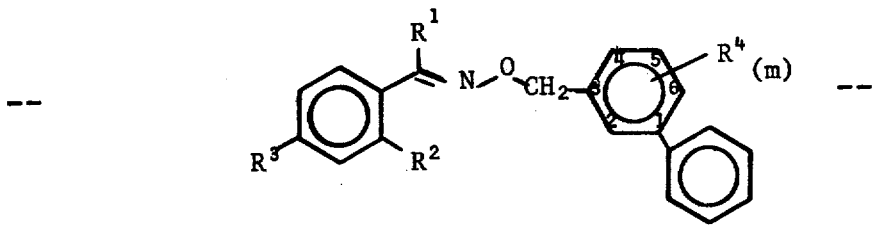

Signed and Sealed this

Thirtieth Day of October 1984

[SEAL]

Attest:

Attesting Officer

GERALD J. MOSSINGHOFF

Commissioner of Patents and Trademarks